United States Patent [19]

McDonnell et al.

[11] Patent Number: 5,498,366
[45] Date of Patent: *Mar. 12, 1996

[54] LIQUID CRYSTAL THIOL COMPOUNDS

[75] Inventors: Damien G. McDonnell; Sally E. Day, both of Malvern; David Coates, Poole; John A. Jenner, Dorset; Michael Hird; Kenneth J. Toyne, both of Hull, all of England

[73] Assignee: The Secretary of State for Defence in her Britannic Majesty's Government of the U.K. of Gt. Britain and Northern Ireland, London, England

[ * ] Notice: The term of this patent shall not extend beyond the expiration date of Pat. No. 5,352,381.

[21] Appl. No.: 260,401

[22] Filed: Jun. 14, 1994

Related U.S. Application Data

[62] Division of Ser. No. 867,739, Apr. 13, 1992, Pat. No. 5,352,381, which is a continuation of PCT/GB9/00932, Jun. 11, 1991, abandoned.

[30] Foreign Application Priority Data

Jun. 11, 1990 [GB]  United Kingdom ................. 9012968

[51] Int. Cl.⁶ ..................... C09K 19/06; C09K 19/12; C09K 19/34; G02F 1/13
[52] U.S. Cl. ................... 252/299.6; 252/299.66; 252/299.61; 359/103
[58] Field of Search ................... 252/299.6, 299.66, 252/299.61; 359/103

[56] References Cited

U.S. PATENT DOCUMENTS

| | | | |
|---|---|---|---|
| 4,348,324 | 9/1982 | Demus et al. ................. | 549/369 |
| 4,943,385 | 7/1990 | Inoue et al. ................. | 252/299.61 |
| 5,043,093 | 8/1991 | Krause et al. ................ | 252/299.61 |
| 5,068,053 | 11/1991 | Reiffenrath et al. .......... | 252/299.61 |
| 5,124,068 | 6/1992 | Krause et al. ................ | 252/299.61 |
| 5,128,061 | 7/1992 | Hsu et al. ................... | 252/299.61 |

FOREIGN PATENT DOCUMENTS

| | | |
|---|---|---|
| 3905932A1 | 9/1989 | Germany. |
| WO86/06401 | 11/1986 | WIPO. |
| WO88/02130 | 3/1988 | WIPO. |

OTHER PUBLICATIONS

J. Phys. Chem. 1990, 94, 1224–1226 Khundkar et al "Solvent–Tuned Intramolecular Charge–Recombination Rates in a Conjugated Donor–Acceptor Molecule".

J. Organometallic Chemistry, 390 (1990) 389–398 Amatore et al "Efficient palladium–catalyzed synthesis . . . ".

Demus et al, Flussige Kristalle in Tabellen II, pp. 373–388, 1984.

Primary Examiner—Richard D. Lovering
Assistant Examiner—C. Harris
Attorney, Agent, or Firm—Nixon & Vanderhye

[57] ABSTRACT

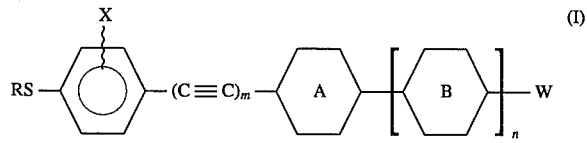

Compounds of formula (I) where R is $C_{1-15}$ alkyl, X is hydrogen, fluorine or chlorine, m and n are independently selected 1 or 0, W is $C_{1-15}$ alkyl or alkoxy, CN or halogen, rings A and B are independently selected from phenyl, laterally fluoro- or chloro- substituted phenyl, transcyclohexyl, pyridyl, pyrimidyl or dioxanyl. Preferred embodiments have $R=C_{3-8}$ and where W is alkyl or alkoxy then it is also preferable that $W=C_{3-8}$. Where m=0, then preferably W=CN, and where m=1, then preferably W=alkyl.

11 Claims, No Drawings

LIQUID CRYSTAL THIOL COMPOUNDS

This is a division of application Ser. No. 07/869,739 filed Apr. 18, 1992, now U.S. Pat. No. 5,352,381, which is a continuation of PCT/GB91/00932, filed Jun. 11, 1991, abandoned.

This invention relates to compounds containing a thiol group and which have liquid crystalline properties and/or which are suitable for use as constituents of liquid crystal materials. The invention also relates to the use of such compounds in liquid crystal materials.

Liquid crystal materials end their use in electro-optical display devices (watches, calculators etc) are well known. The most commonly Used type or liquid crystal material is that which shows a nematic (N) phase, and such materials are widely used in known types of liquid crystal electro-optical display device such as the Twisted Nematic (TN) device, Supertwist Nematic (STN) device, Electrically Controlled Birefringence (ECB) device.

Liquid crystal materials are generally mixtures of compounds which individually or together show a liquid crystal phase. A number of desirable characteristics are sought in such compounds and materials. Among these are chemical stability, persistence of nematic liquid crystal phases over a wide temperature range preferably including room temperature, and for some types of device a high birefringence ($\Delta n$) is sought.

A class of compounds which is widely used in such materials are the alkyl and alkoxy cyanobiphenyls end terphenyls:

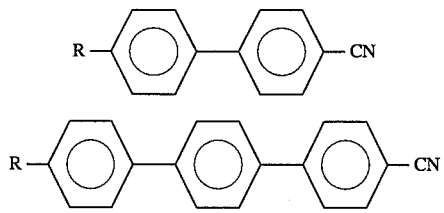

where R is alkyl or alkoxy. These are useful liquid crystalline compounds but for some applications their low birefringence limits their value.

It is an object or the present invention to provide compounds and materials having at least some of these desirable characteristics, and in particular a high birefringence.

According to this invention, novel compounds of Formula I are provided:

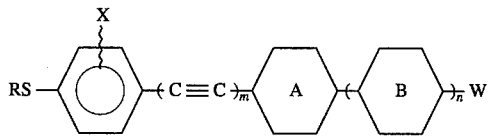

wherein R is $C_{1-15}$ alkyl, X is hydrogen, fluorine or chlorine, m and n are independently 1 or 0, W is $C_{1-15}$ alkyl or alkoxy, CN or halogen, rings A and B are independently selected from phenyl, laterally fluoro- or chloro-substituted phenyl, trans-cyclohexyl, pyridyl, pyrimidyl or dioxanyl rings.

The structural and other preferences expressed below are on the basis of inter alia ease of preparation, desirable liquid crystalline characteristics in particularly high birefringence, or other suitability for use in liquid crystal materials.

Preferably R is $C_{3-8}$ alkyl. If W is alkyl or alkoxy it preferably contains 3–8 carbon atoms. Preferably rings A and B (if present) are phenyl. Preferably n is zero. Preferably X is hydrogen or fluorine. Preferably if m is 0 W is CN and if m is 1 W is alkyl. Alkyl or alkoxy groups W are preferably straight chain or asymmetrically branches, preferred branched groups being 2-methylbutyl or 2-methylbutyloxy. The presence of such asymmetric groups in the molecule induces the formation of chiral nematic (cholesteric) liquid crystal phases.

Overall preferred structures for compounds of Formula I are those listed below:

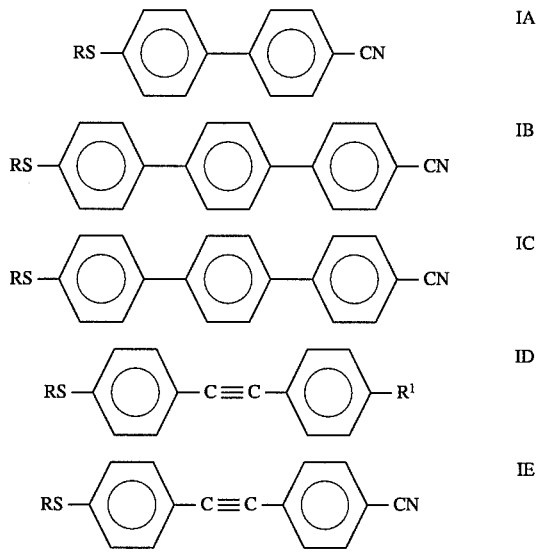

and analogues thereof in which one or more of the phenyl rings is mono- or di-fluorinated. $R^1$ is alkyl or alkoxy.

Of these structures IA and ID are particularly preferred. The presence of the thiol group leads to compounds having a high birefringence.

Compounds of Formula I may be prepared by various routes which will be apparent to those skilled in the art. A preferred route to compounds in which m is o and A is aromatic, especially in which W is cyano, such as IA, IB or IC is that which involves coupling between the appropriate phenyl 4-bromo or iodo alkylthiol:

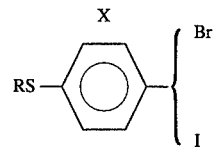

and the appropriate boronic acids:

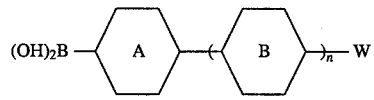

mediated by a palladium (o) catalyst, eg tetrakis (triphenylphosphine) palladium (o) ("TTPP"). Methods of preparing such thiols end boronic acids ape well known, for example a method of preparing such a boronic acid from a corresponding bromophenyl system and an alkyl borate is described inter alia in WO89/12621. Suitable conditions for the coupling reaction ape also well known.

To prepare corresponding compounds in which one or mope of the rings A and B and the phenyl ring is/ape laterally substituted, the correspondingly substituted starting compounds are used. The coupling reactions described above are generally not affected by the presence of the substituents most commonly used in liquid crystal compounds, eg fluorine and chlorine. For example fluorinated boronic acids of Formula:

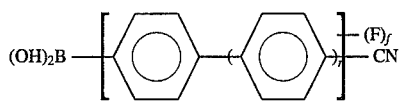

wherein f is 1 or 2 may be prepared from 4-bromo/iodo fluoro berzonitriles or cyanobiphenyls to enable preparation of fluorinated analogues of Formula IA and IB. eg

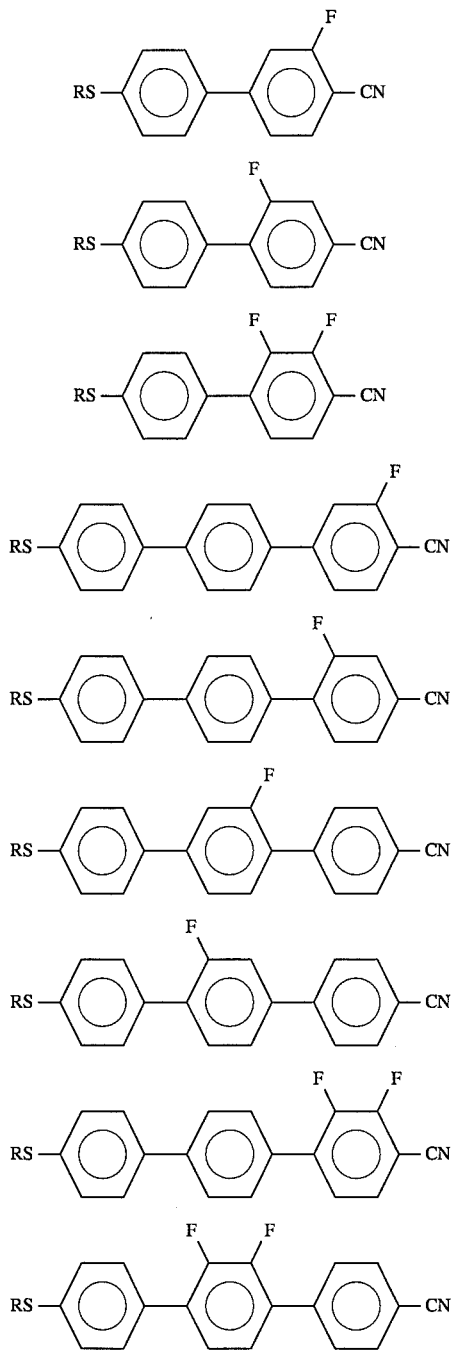

Such benzonitriles and cyanobiphenyls are known or may be prepared by coupling of smaller units using the boronic acid—bromo/iodo phenyl coupling method referred to above. For example starting from known 2-fluoro-4-bromobenzonitrile and para-iodobromobezene, and exploiting the greater affinity of the boronic acid for the iodine substituent:

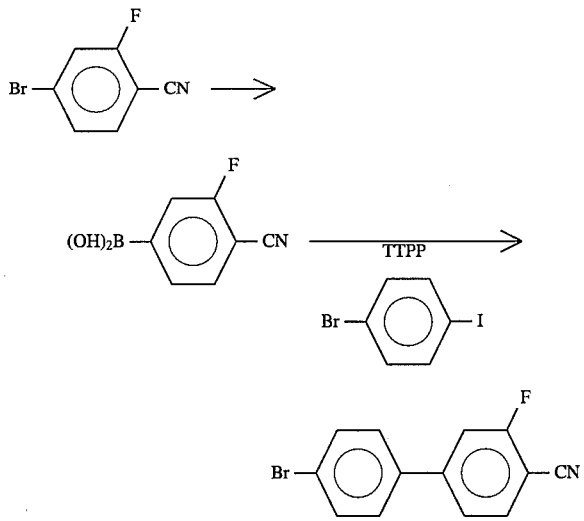

Compounds in which m is 1 and A is aromatic especially phenyl or substituted phenyl may be prepared by coupling, via elimination of HBr, between an appropriate phenyl 4-bromo or iodo alkylthiol as above and an appropriate ethine:

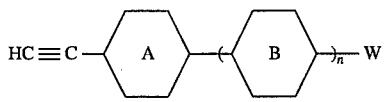

This method is particularly suitable for preparation of compounds such as ID in which W alkyl.

When ring A is phenyl or substituted phenyl these ethines may be prepared via the corresponding acetophenone using a generally known dehydrohalogenation route eg:

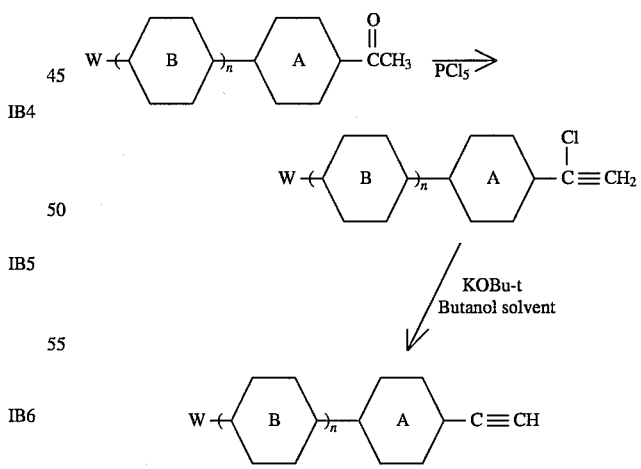

Methods of preparing acetophenones are well known, eg Friedel Krafts acylation.

The ethine may be coupled with the thiol using a coupling reaction in which the ethine group is coupled with a halo (bromo- or preferably iodo-) benzine in a reaction mediated by a paliadium (0) catalyst, for example:

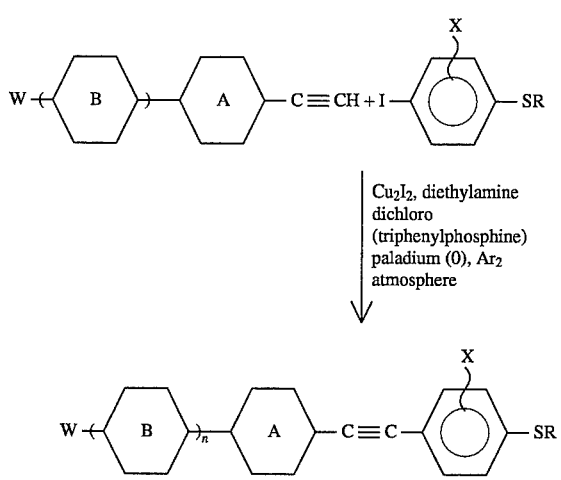

Other suitable ethines in which ring A is aromatic may be prepared using generally known methods for example that exemplified by route A of GB 9000965.5 in which a corresponding bromo- or iodo- compound of Formula:

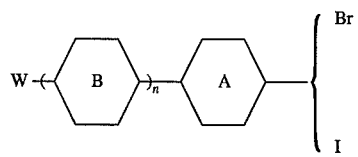

is reacted with lithium acetylide ethylene diamine complex and zinc chloride. Another method of preparing suitable ethines using such bromo- or iodo compounds is step IC of WO89/08102. Many bromo- and iodo- compounds of the immediately above Formula are known or may be synthesised with relative ease, including those with lateral substituents such as fluorine. For example compounds of Formula:

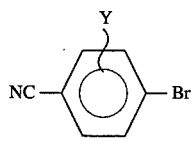

are known (w=cyano, h=o, y=fluorine or hydrogen), enabling preparation of the corresponding ethine and then compounds of Formula IEI:

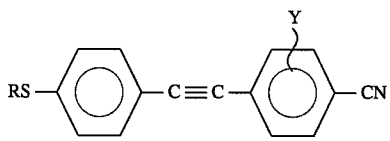

Other methods of preparing compounds of Formula I will be apparent to those skilled in the art.

A further aspect of this invention is a liquid crystalline material, containing at least two components, at least one of which is a compound of Formula I. This liquid crystalline material is preferably a nematic or cholesteric liquid crystalline material. Such materials may be used in electro-optic display devices such as watches and calculators etc, and also in thermochromic displays in which the colour of reflected light varies with temperature.

Compounds of Formula I, in particular the preferred compounds referred to above, have a number of desirable properties which make them very useful components of liquid crystal materials, in particular their high birefringence.

Suitable compounds for the other components of the liquid crystal material will be apparent to those skilled in the field, and will depend upon the properties such as dielectric anisotropy, birefringence, working temperature range etc required in the material for the application for which the material is intended. Some types of suitable material are discussed briefly below.

Preferably as well as containing one or more Formula I compounds the mixture contains one or more compounds of Formula II:

wherein $R_b$ is alkyl or alkoxy, preferably containing 1 to 8 carbon atoms, and preferably straight chain, and wherein m is 0 or 1. Such compounds are included in the subject matter of GB 1433130. The material may for example contain other liquid crystalline compounds which have a positive dielectric anistropy, for example as described in EP-A-0132377, particularly in FIG. 8 thereof and the related text.

The material may alternatively or also contain liquid crystalline compounds of low dielectric anistropy, for example to form a mixture of intermediate dielectric anistropy, or a thermochromic mixture. Some examples of such compounds are described in EP-A-0132377, particularly in FIG. 9 thereof and the related text.

The material may alternately or also contain liquid crystalline compounds having a high clearing point, for example to raise the N-I transition temperature. Some examples of such compounds are described in EP-A-0132377, particularly in FIG. 10 thereof and the related text.

To cause the material of this aspect of the invention to show a cholesteric (Ch) (or chiral nematic) phase the material must contain at least one compound containing an asymmetric carbon atom. This may be a chiral compound of Formula I, or alternatively or also the material may for example contain one or more chiral compound of Formula II above, eg (+) or (−) 4-(2-methylbutyl)-4'-cyano biphenyl or 4-(2-methylbutyloxy)- 4'cyano biphenyl.

The material may also contain one or more pleochroic dyes, for example the dyes described in EP-A-82300891.7.

The proportions of these components used in the material of this aspect of the invention will depend upon the intended application, and the material may usefully contain two or more compounds of Formula I. If the material does contain two or more compounds of Formula I there may be in proportions that are, or approximate to, a eutectic mixture.

The materials of this aspect of the invention may be used in any of the known forms of liquid crystal display device, for example a twisted nematic effect device, Freedericks effect device, cholesteric memory mode device, cholesteric to nematic phase change effect device, dynamic scattering effect device, two frequency switching effect device, a "supertwist" effect device, or a thermometer using a thermochromic material. The method of construction and operation of such devices, and characteristics of a liquid crystal material suitable for use therein, are well known in the field. A liquid crystal display device which incorporates as its working fluid a material as described above, constitutes another aspect of this invention.

Non limiting examples illustrating this invention will now be given. The abbreviations K=solid crystal, I=isotropic liquid are used.

EXAMPLE 1

Preparation of:

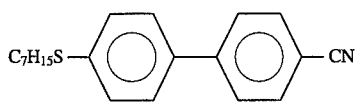

1.1 4-n-heptylthiobromobenzene

4-Bromothiophenol (15 g, 0.0794 m) was stirred and heated at 80° C. for 18 hours with n-heptylbromide (14.9 g, 0.0833 m) sodium hydroxide (3.3 g, 0.0833 m) and water (15 mls). The mixture was then added to water (50 mls) and extracted with petroleum spirit 400°–60° (3×50 mls). The combined organic phase was dried over magnesium sulphate and evaporated to yield 4-n-heptylthiobromobonzene (19.5 g, 89% GLC, 85% yield).

1.2 4-cyanophenylboronic acid

4-Bromobenzonitrile (20 g, 0.1099 m) was dissolved in tetrahydrofuran (240 mls) and hexane (80 mls) and the mixture treated with butyl-lithium (1.6M solution in hexame 80 mls, 0.1204 m) at −100° C. The mixture was then stirred for five minutes before adding trimethyl berate (25 mls, 0.2178 m) at −100° C. The mixture was then allowed to warm to 20° C. before adding it to 100 mls of 10% HCL. The organic layer was then separated and the aqueous layer extracted twice with dichloromethane (100 mls). The organic layers were then combined and washed till acid free with water. The solution was then dried using magnesium sulphate and evaporated to give 4-cyanophenyl boronic acid as an off-white solid (15 g 93% yield) which was dried under vacuum.

1.3 4-cyano-4'-heptylthiobiphenyl

4-Cyanophenylboronic acid (7 g, 0.0476 m) was stirred and refluxed for 60 hours under nitrogen with 4-n-heptylthiobromobenzene (12.4 g, 0.0433 m), TTPP (0.9 g, 0.000783 m), 2 molar aqueous sodium carbonate (41 mls). toluene (86 mls) and industrial methylated spirit (20.5 mls). The mixture was then separated and extincted with toluene (2×100 mls) washed with water (100 mls) and dried over magnesium sulphate. The solvents were then evaporated off to give a brown solid products which was purified by column chromatography and recrystallisation from industrial methylated spirit. 4-Cyano-4'-heptylthiobiphenyl was produced (4.1 g, 100% HPCL, 30% yield melting point 64.4° C.).

Homologues of this compound were prepared having different 4'-alkyl termini. These had the properties below:

| R(n) | K-I° C. | Δ H(K Cals/Mole) |
| --- | --- | --- |
| $CH_3$ | 131.5 | — |
| $C_4H_9$ | 63.8 | 7.27 |
| $C_5H_{11}$ | 53.0 | 7.62 |
| $C_6H_{13}$ | 61.6 | 7.54 |
| $C_7H_{15}$ | 64.4 | 11.31 |

An approximately eutectic mixture containing the butyl, pentyl, hexyl and heptyl compounds in wt % proportions 26.3, 34.6, 26.9, 12.2 respectively was prepared. This showed K-I 41°–0° C. and N-I (34.5° C.) but crystallised too readily to measure Δn at 20° C. 10 wt % of 4'-n-pentyl-4-cyanobiphenyl was added to this eutectic which resulted in K-I of 34.5° C. and N-I of (34.2° C.). The birefringence of this mixture at 20° C. was 0.222 which is substantially higher than that of the cyanobiophenyl itself (0.19).

EXAMPLE 2

Preparation of:

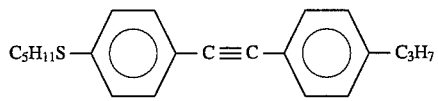

Step 2.1 4-n-pentylthiobromobenzene

A mixture of 4-bromothiophenol (30 g), pentyl bromide (26.4 g), sodium hydroxide (6.67 g) and water (30 ml) was heated at 90° C. and stirred for 48 hrs. The mixture was then poured into water, extracted with petroleum spirit, dried and distilled (bp 96° C. at 0.11 mmHG). Yield 27.3 g.

Step 2.2 4-n-pentylthioiodobenzene

The Grignard reagent from the product of Step 2.1 (15 g) was prepared using magnesium in tetrahydrofuran (60 ml). Iodine (16.2 g) was added over 10 min and the mixture was stirred for 16 hrs. Water was added and then 10% sodium metabisulphite (100 ml). The product was extracted into petroleum ether and distilled. Yield 10.5 g.

Step 2.3 1-(4-n-propylphenyl)-1-chloroethylene

Phosphorous pentachloride (51.4 g) was slowly added to stirred 4-n-propylacetephenone (40 g) at 35°–45° C. After addition the mixture was heated to 70° C. for 3 hrs and then slowly poured into ice/water, extracted with petroleum ether and distilled, (bp 67° C. at 0.65 mmHg). Yield 20.2 g.

Step 2.4 4-n-propylphenyl ethine

Potassium t-butoxide (21.5 g) was added to stirred t-butanol and warmed to gentle reflux. The alkene product from step 2.3 (20 g) was added dropwise and then the mixture was heated under reflux for 3 hrs. Water (100 ml) was added and the product extracted into petroleum spirit (3× 100 ml), washed with 10% HCl and water. The crude alkine product was 97% pure by gc. Yield 12 g.

Step 2.5 1-(4-n-propylphenyl)-2-(4-n-pentylthiophenyl)-ethine

The product from step 2.4 (2.82 g) and the product from step 2.2 (6.0 g) were mixed in diethylamine (44 ml). Copper (I) iodide (0.026 g) and dichloro di(triphenylphosphine) palladium (0) (0.193 g) were then added and the mixture was then stirred at 20° C. under argon for 16 hrs. Purification by chromatography gave 4.3 g or tolane product, rapt. 43° C.

Measurement of (Δα/α), where α is polarisability of the compound, can be made by Abbe refractometry of the compounds of Formula I in mixture with another compound. Typical compounds suitable for mixing include non-polar I compounds and polar ZLI1132 (Merck, West Quay Road, Poole, Dorset, BH15 1HX, Great Britain). Use of such mixtures induce a wide nematic temperature range.

Use of Abbé refractometry provides measurement of the extraordinary and ordinary refractive indeces, $n_e$ and $n_o$ respectively. (Δα/α) is determined from extrapolation of temperature depence of $(n_e^2-n_o^2)/(\bar{n}^2-1)$ using a Haller plot. The technique may be used for compounds with little or no inherent nematic phase by extrapolation from values obtained at low concentrations of compounds of Formula I in the host nematic material.

Δα can be derived from Δα/α measurements using standard expressions for α and refractive indeces. For convenience, normalization of can be expressed relative to other known liquid crystal compounds.

can also be used to calculate a figure of merit, $A_1$, for compounds of Formula I, where $A_1$ is given by $$A_1 = \frac{2(\Delta\alpha)^2 LP}{15a}$$

where

Δα=anisotropy in polarisation,

L=local field factor, p=number density a=anisotropy in the inter-molecular field potential.

$A_1$ can also be measured by degenerate four wave mixing (eg P. A. Madden, F. C. Saunders and A. M. Scott, IEEE J of Quantum Electronics Vol QE22 No 8 Aug. 1986 pp1287–1297).

Table 1 gives values of Δα relative to 4-cyano-(4'pentyl)-1-phenyl-cyclohexane (5PCH).

TABLE 1

| Compound | (of 5PCH) |
|---|---|
| 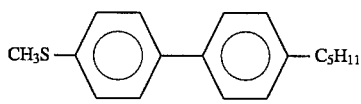 C₄H₉S—⟨ ⟩—⟨ ⟩—CN | 2.91 |
| C₆H₁₃S—⟨ ⟩—⟨ ⟩—CN | 3.46 |
| C₅H₁₁S—⟨ ⟩—⟨ ⟩—CN | 2.81 |

Typically, a compound such as

CH₃S—⟨ ⟩—⟨ ⟩—C₅H₁₁ has a calculated $A_1$ (from Abbe refractometry at a wavelength of 589 nm and relative to $C_5$ alkylcyanobiphenyl) of 1.03.

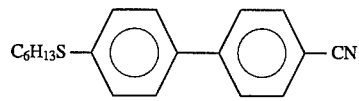
C₆H₁₃S—⟨ ⟩—⟨ ⟩—CN has a calculated $A_1$ from Abbe refractometry at 1 um and relative to $C_5$ alkylcyanobiphenyl) of 1.6 whilst having a measured $A_1$ (from degenerate four wave mixing) of 1.05.

We claim:

1. A liquid crystal mixture including at least one compound of formula I:

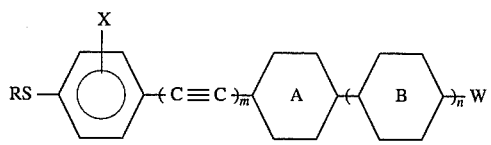

wherein R is $C_{1-15}$ alkyl, X is hydrogen, fluorine or chlorine, m and n are independently 1 or 0, W is $C_{1-15}$ alkyl or alkoxy, CN or halogen, rings A and B are independently selected from phenyl, laterally fluoro- or chloro-substituted phenyl, trans-cyclohexyl, pyridyl, pyrimidyl or dioxanyl; provided A or B is not pyrimidine when m=0, X=H, W=alkyl or alkoxy and whichever of A or B is not pyrimidine is phenyl; and excluding m=1 when n=0, A=phenyl, W=alkyl, X=H.

2. A mixture according to claim 1 wherein rings A and B, if B is present, are phenyl.

3. A mixture according to claim 1 or claim 2 wherein m is 0 and W is CN.

4. A mixture according to claim 3 having the formula:

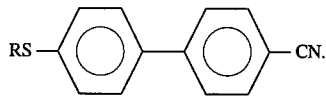

5. A mixture according to claim 3 having a formula selected from:

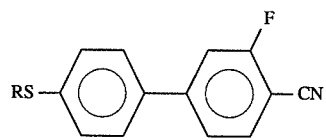

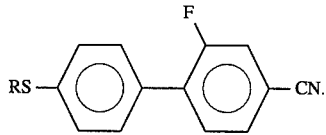

6. A mixture according to claim 1 or 2 wherein m is 1.

7. A mixture according to claim 6 having a formula:

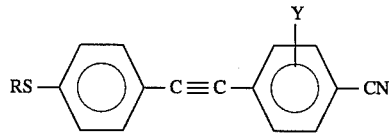

where Y is fluorine or hydrogen.

8. A liquid crystalline mixture according to claim 1 wherein the liquid crystalline mixture is nematic.

9. A electro-optical device comprising two spaced cell walls each bearing electrode structures, and a layer of material enclosed between the cell walls, wherein the material comprises a mixture of claim 1.

10. An optical device comprising two spaced cell walls each bearing electrode structures, and a layer of material enclosed between the cell walls, wherein the material comprises a mixture of claim 1.

11. An optical device comprising two spaced cell walls and a layer of material enclosed between the cell walls, wherein the material comprises a mixture of claim 1.

* * * * *